US012053562B2

(12) United States Patent
Magee

(10) Patent No.: US 12,053,562 B2
(45) Date of Patent: Aug. 6, 2024

(54) CORONAVIRUS (COVID-19) AIR SANITIZATION/ISOLATION SYSTEM WITH ANTI-VIRUS CURTAIN WALLS

(71) Applicant: Florida A&M University, Tallahassee, FL (US)

(72) Inventor: Charles Magee, Cairo, GA (US)

(73) Assignee: FLORIDA A&M UNIVERSITY, Tallahassee, FL (US)

( * ) Notice: Subject to any disclaimer, the term of this patent is extended or adjusted under 35 U.S.C. 154(b) by 465 days.

(21) Appl. No.: 17/392,395

(22) Filed: Aug. 3, 2021

(65) Prior Publication Data

US 2022/0040354 A1 Feb. 10, 2022

Related U.S. Application Data

(60) Provisional application No. 63/060,890, filed on Aug. 4, 2020.

(51) Int. Cl.
| | |
|---|---|
| *A61G 10/00* | (2006.01) |
| *A61L 9/03* | (2006.01) |
| *A61L 9/20* | (2006.01) |
| *A61L 9/22* | (2006.01) |

(52) U.S. Cl.
CPC ............ *A61L 9/032* (2013.01); *A61G 10/005* (2013.01); *A61L 9/037* (2013.01); *A61L 9/20* (2013.01); *A61L 9/22* (2013.01); *A61L 2209/134* (2013.01); *A61L 2209/14* (2013.01); *A61L 2209/213* (2013.01)

(58) Field of Classification Search
CPC . A61L 9/032; A61L 9/037; A61L 9/20; A61L 9/22; A61L 2209/134; A61L 2209/14; A61L 2209/213; A61L 2/10; A61L 2/16; A61L 2/18; A61G 10/005

See application file for complete search history.

(56) References Cited

U.S. PATENT DOCUMENTS

| | | | | |
|---|---|---|---|---|
| 5,429,404 A * | 7/1995 | King, Sr. | .................. | E06B 3/80 160/DIG. 16 |
| 6,162,118 A * | 12/2000 | Arts | ........................ | F24F 3/163 135/93 |
| 2015/0327706 A1* | 11/2015 | Harter | .................... | A47H 23/08 160/126 |
| 2021/0322242 A1* | 10/2021 | Hogan | ................. | A61G 10/023 |

* cited by examiner

*Primary Examiner* — Timothy C Cleveland
(74) *Attorney, Agent, or Firm* — Greenberg Traurig, LLP

(57) ABSTRACT

Various embodiments are directed to a coronavirus air sanitization/isolation system with anti-virus curtain. The system may include a group of anti-virus strips with attached separation magnets coupled to an air inlet housing mounted above (e.g., in an attic ceiling) in an enclosed space. The anti-virus strips may be coated with a saline and soap solution that attracts airborne droplets contaminated with the coronavirus and dissolves a fatty layer of coronavirus cell membranes to prevent cell replication of the coronavirus, thereby destroying the coronavirus. The air inlet housing may include exhaust ventilation fans, salt filters, a wick saturated with the saline and soap solution, an electro-static air filter, and a distribution air duct. The fans may be utilized to circulate an airstream containing the coronavirus through the anti-virus strips, the filters, the saturated wick, and the distribution air duct to remove the coronavirus while protecting occupants with uncontaminated air.

13 Claims, 5 Drawing Sheets

CORONAVIRUS (COVID-19) AIR SANITIZATION/ISOLATION SYSTEM WITH ANTI-VIRUS CURTAIN WALLS

CROSS REFERENCE TO RELATED APPLICATION

This application claims the benefit of U.S. Provisional Application No. 63/060,890, filed Aug. 4, 2020, the disclosure of which is incorporated, in its entirety, by this reference.

BACKGROUND

The world is currently in the midst of the worse pandemic in more than 100 years due to the coronavirus (COVID-19) which is a contagious disease caused by severe acute respiratory syndrome coronavirus 2 (SARS-CoV-2). While there are currently experimental vaccines available protecting persons from becoming sick from COVID-19, there is still uncertainty withing the medical community regarding their effectiveness in preventing transmission of the virus. Furthermore, at the present time there is no known cure and it has become evident that COVID-19 will persist for a very long time. The spread of COVID-19 is often particularly problematic when people are in enclosed spaces. For example, in many enclosed spaces, occupants often inhale airborne droplets from infected individuals (e.g., via coughing or sneezing) that may be carried by recirculated air distributed from indoor ventilation systems. In conventional enclosed spaces, airborne (e.g., COVID-19) droplets generated by infected individuals may be propelled forward at least six to eight feet and remain airborne for several minutes (e.g., a minimum of six minutes), thereby creating an environment facilitating the spread of viruses when people are in close contact with each other. Additionally, COVID-19 may also be potentially spread by the touching of contaminated surfaces in which case the virus may be transferred through the touching of the mouth, nose, or eyes. As in the case of airborne spread, exposure to the virus is more likely when people are in close contact with each other (e.g., within six to eight feet).

Traditional solutions for mitigating the spread of COVID-19 within enclosed spaces include requiring social distancing measures in which persons gathered in enclosed spaces are separated by a minimum of six feet. However, in many professions and industries, such as education, healthcare, and transportation, close contact between individuals may be impracticable or unavoidable. For example, social distancing may be difficult to maintain between teachers and/or students in a small classroom, between doctors and patients in offices and hospital waiting rooms, and between drivers and riders/passengers utilizing public and private transportation services (e.g., buses, subways, taxis, ridesharing, etc.).

SUMMARY

As will be described in greater detail below, the instant disclosure generally relates to a COVID-19 air sanitization/isolation system with anti-virus curtain walls. In one example, the system may include a group of anti-virus strips coated with a saline and soap solution. Salt molecules within the saline and soap solution attract airborne droplets contaminated with COVID-19 (hereinafter referred to interchangeably as "the coronavirus" or "the virus") onto a surface of the anti-virus strips and soap molecules within the saline and soap solution react with the airborne droplets to dissolve a fatty layer of coronavirus cell membranes, thereby destroying the coronavirus.

The system may further include a group of magnets arranged vertically along a length of an inner surface on each of the anti-virus strips. Like poles of a first magnet in the group of magnets may be arranged to face like poles of an opposing magnet on each of the anti-virus strips. The magnets assist in preventing the anti-virus strips from encountering (e.g., coming into contact with) each other.

The system may further include an air inlet housing coupled to a first subset of the anti-virus strips. The inlet housing may be configured to vertically suspend the first subset of the anti-virus strips as a parallel wall of curtains within an interior of an enclosed space. The air inlet housing may include (1) a first exhaust ventilation fan that utilizes suction to pull air from at least an exterior of the enclosed space into an interior of the enclosed space as an airstream comprising contaminated airborne coronavirus droplets, (2) a first salt filter that receives the airstream from the first exhaust ventilation fan, (3) a wick saturated with the saline and soap solution that receives the airstream from the first salt filter, (4) a second salt filter below the first exhaust ventilation fan that receives the airstream from the first exhaust ventilation fan, (5) an electro-static air filter below the second salt filter that receives the airstream from the second salt filter, (6) a second exhaust ventilation fan below the electro-static air filter that receives the airstream from the electro-static air filter, (7) a distribution air duct below the second exhaust ventilation fan that receives the airstream from the second exhaust ventilation fan, where the distribution air duct includes a group of air jet slots spaced along a length of the distribution air duct, where the air jet slots distribute the airstream as a group of two-dimensional free jets, and where the distribution air duct may include an ultra-violet (UV) light source that generates UV radiation for disinfecting one or more contaminated surfaces in the enclosed space, and (8) a second subset of the plurality of anti-virus strips coupled to the distribution air duct and vertically suspended between each of a pair of opposing air jet slots in the plurality of air jet slots, where the second subset of the plurality of anti-virus strips face each of the one or more persons in the enclosed space for intercepting contaminated airborne coronavirus droplets expelled from the one or more persons in the enclosed space.

In some examples, the system may additionally include a second group of UV light sources mounted within a ceiling of the enclosed space and proximate to the distribution air duct for generating UV radiation that disinfects the contaminated surfaces in the enclosed space only when the persons occupying the enclosed space have exited the enclosed space. In some examples, the saline and salt solution on the surface of the anti-virus strips draws, via osmosis, water from the airborne droplets contaminated with the coronavirus.

In some examples, the dissolved fatty layer of the coronavirus cell membranes by the soap molecules prevent cell replication of the coronavirus. In some examples, any remaining airborne droplets in the airstream that are not attracted to the surface of the anti-virus strips are drawn into the first exhaust ventilation fan. In some examples, the saline and soap solution saturate the wick, heat in the airstream evaporates water in the wick, and the evaporated water molecules raise the relative humidity of the airstream. In some examples, the second salt filter, upon receiving the saturated airstream from the first exhaust ventilation fan, lowers the relative humidity of the airstream.

In some examples, the electro-static filter, upon receiving the airstream from the second salt filter, removes salt residue particles, dust particles, and/or spores from the airstream. In some examples, the UV light source only generates the UV radiation for disinfecting the one or more contaminated surfaces in the enclosed space when the airstream is flowing through the air inlet housing.

In some examples, each of the free jets is made up of distributed air that envelops each of the one or more persons occupying the enclosed space within an uncontaminated zone of air. In some examples, the free jets are converted into wall jets upon coming into contact with the anti-virus strips. In some examples, the second subset of the group of anti-virus strips intercept the contaminated airborne coronavirus droplets by receiving coughs and/or sneezes expelled from the one or more persons occupying the enclosed space.

In some examples, the parallel wall of curtains surrounds a substantial portion of the enclosed space and the enclosed space may be having a ceiling, a floor, and two pairs of opposing sides. In other examples, the enclosed space may be a vehicle including a roof, a floor, and two pairs of opposing sides. In some examples, the air inlet housing may be installed in an attic above a ceiling of the enclosed space that is located in a building.

In some examples, the system described herein may be utilized in an enclosed space containing other viruses, bacteria, and/or spores. That is, the system described herein may be utilized to kill or destroy bacteria, viruses, and spores at multiple locations within the system.

Features from any of the above-mentioned embodiments may be used in combination with one another in accordance with the general principles described herein. These and other embodiments, features, and advantages will be more fully understood upon reading the following detailed description in conjunction with the accompanying drawings and claims.

DETAILED DESCRIPTION

Figure 1:
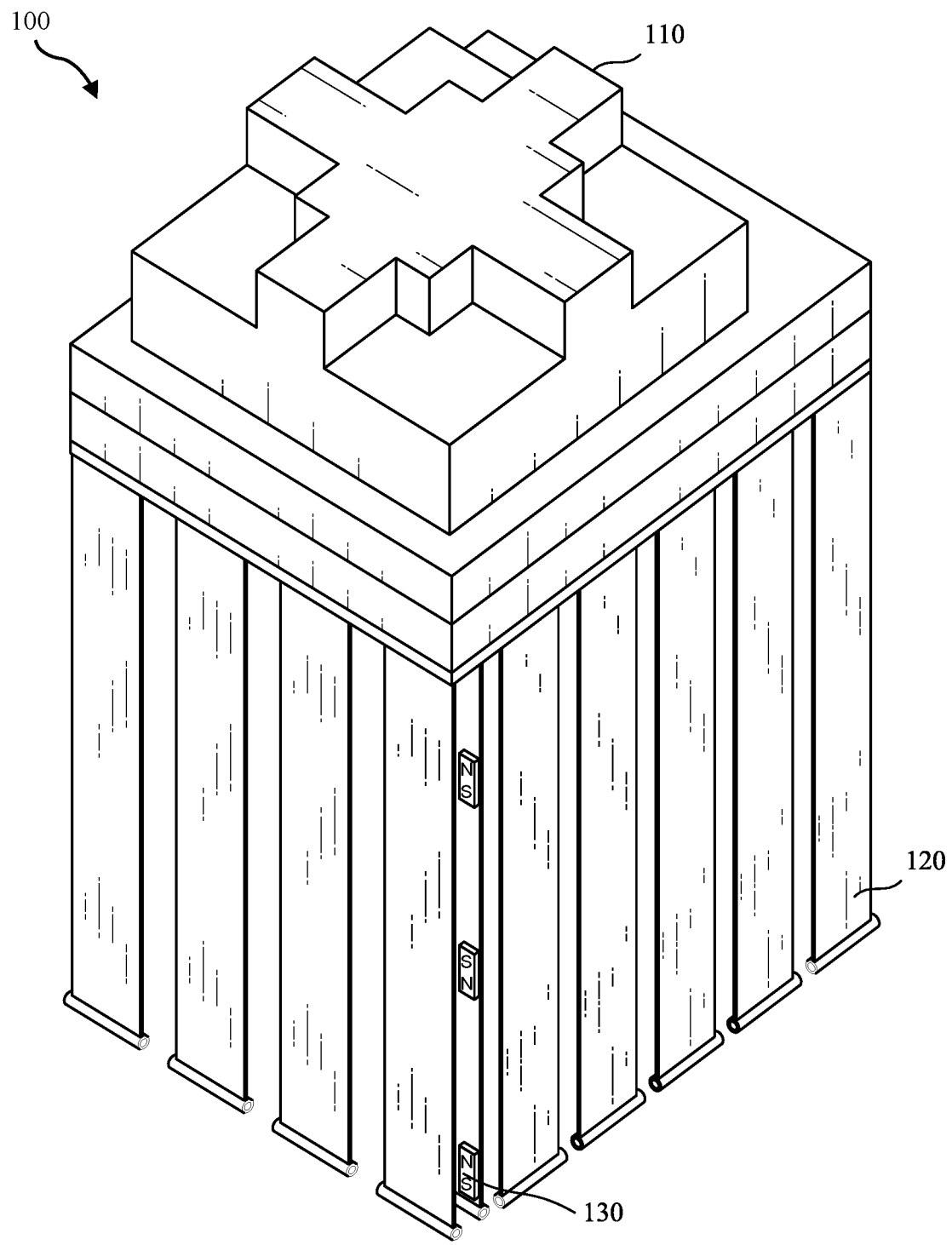
FIG. 1 illustrates a perspective view of a coronavirus air sanitization/isolation system with anti-virus curtain walls, according to an example embodiment.

The present disclosure is generally directed to a coronavirus (COVID-19) air sanitization/isolation system with anti-virus curtain walls. In particular, the system described herein includes components that may mitigate the person-to-person spread of COVID-19, when people are occupying enclosed spaces. As an example, in an enclosed space, when a person sneezes or coughs, the airstream leaving their nose or mouth is analogous to an air jet exiting an inlet of a ventilated structure under a negative pressure. An air jet is defined as a region of air moving at a velocity different from the velocity of the surrounding air. If the air jet is directed away from all boundaries of a room, it is a free jet. If it is directed to flow along a wall or ceiling, it is a wall jet. A free jet, if it approaches a solid boundary, will attach to the boundary and become a wall jet. A wall jet will remain a wall jet until it encounters a large solid obstacle or unless thermal buoyancy forces are so great that its current direction is changed. The phenomenon which keeps a jet attached to a solid boundary is termed the "Coandă effect."

In accordance with various embodiments described herein, the system may address two main modes of spreading the coronavirus: (1) by inhaling airborne droplets of the virus from an infected individual, and (2) by touching a surface contaminated by an infected individual (i.e., a contaminated surface) and transferring the virus by way of touching the mouth, nose, or eyes. In addition, the spreading of the virus is often much more likely when people are in close contact with each other (e.g., within six to eight feet). Moreover, and as will be described in greater detail below, the system utilizes a method of distributing soap molecules that dissolve the fatty outside layer of the coronavirus (which envelops the nucleocapsid made of protein) and therefore destroy it before it has had a chance to replicate by inserting itself into living cells. For example, the system may provide anti-virus strips that are laced with a combined saline and soap solution to draw in airborne droplets. In particular, salt contained in the saline portion of the solution (which has an affinity for water vapor) acts to attract the airborne droplets from ambient air containing water vapor. Additionally, the soap portion of the solution acts to dissolve the fatty substance of any coronavirus molecules contained in the airborne droplets.

As an example, when inlet air is drawn into air curtains made up of the anti-virus strips, virus droplets become attached. Then, via osmosis, water is drawn from the droplets and viruses in the air such that soap molecules will activate and dissolve the fatty layer of the virus. Those droplets that do not attach to the curtain made up of the anti-virus strips continue to travel in the inlet airstream. The inlet airstream may then be drawn through a salt filter to reduce the airstream's moisture content and relative humidity. After exiting the salt filter, the airstream may then be drawn through a perimeter wick soaked with the combined saline and soap solution. As discussed above, this solution will destroy any viruses remaining in the airstream and also raises the airstream's relative humidity via evaporation of water molecules. The system may further include an exhaust fan. Air exiting the exhaust fan may serve as the inlet airstream for a second exhaust fan after passing through a second salt filter to lower the airstream's relative humidity. Upon exiting the second salt filter, the airstream may then pass through an electro-static air filter to remove any residue salt particles, dust particles, and spores. The airstream exiting the second exhaust fan may then passes through ultraviolet (UV) light before entering a distribution air duct.

In the system described herein (and as will be described in greater detail below), the distribution air duct may function to distribute air in the form of multiple small two-dimensional free jets. Each free jet may serve as a partition wall to separate individual persons (e.g., individual persons seated at a table) within an enclosed space such that each person would essentially have his or her own cubical of uncontaminated air space. Should a seated person sneeze or cough, contaminated droplets would project forward and attach to the saline and soap laced anti-virus strips hanging from the distribution air duct. Then, via osmosis, water would be drawn from the droplets and the virus would react with the soap molecules on the anti-virus strips. The soap solution would then dissolve the fatty layer of the virus. As the free jets (e.g., the airstream) passes seated (or standing) persons in the enclosed space, they will be drawn into the inlet of the air curtain wall (i.e., the air curtains) where they become wall jets on contact and subsequently flow up the air curtain wall due to the Coandă effect. Thus, the system described herein may provide a recirculation cycle that is constantly repeated from the air in the enclosed space that surrounds the system itself.

By utilizing the system as described above, various advantages may be realized for mitigating person-to-person spread of the coronavirus in professions and industries where social distancing may not be achieved and physical separation is needed or required. These advantages may include, without limitation, (1) mitigating the spread of the coronavirus from person to person in enclosed spaces such as classrooms, restaurants, bars, and night clubs, (2) destroying airborne coronaviruses in enclosed spaces, (3) permitting constant sanitization of recirculated air in an enclosed space, (4) isolating health care workers from sick patients, and sick patients from each other, (5) allowing vehicle drivers (e.g., bus drivers) to be isolated from their passengers, (6) allowing teachers to be isolated from their students, (7) allowing persons seated at a table to be shielded from the airborne droplets of coughs or sneezes, (8) allowing a single large open space such as those found in gyms, banquet halls, cafeterias, and classrooms to be partitioned off into isolated spaces, (9) preventing or reducing contraction of the coronavirus in assembly line workers, (10) sanitizing a large volume of air quickly, (11) entraining exterior and interior air through anti-virus curtain walls, (12) enabling retrofitting to almost any space that lacks adequate ventilation, (13) enabling suspension (using suspension cables) from a ceiling or standing alone on the floor, (14) isolating bartenders from their customers, (15) enabling the self-disinfection of surfaces within the system, (16) portability and ease of maintenance and assembly, (17) reducing required social distancing space in a room, (18) providing isolated spaces in field hospitals, and (19) making it easier to quarantine infected patients.

Embodiments of the disclosure now will be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

FIG. 1 illustrates a perspective view of a coronavirus air sanitization/isolation system with anti-virus curtain walls 100 (hereinafter referred to as "system 100"). System 100 may include a group of anti-virus strips 120. Each anti-virus strip 120 may also have attached, a set of separation magnets 130. In some examples, anti-virus strips 120 may surround an enclosed space (i.e., as an anti-virus curtain wall) and be installed within an attic 110 of a building containing the enclosed space. In some examples, the anti-virus strips 120 may be installed in an offset parallel manner along each wall of an enclosed space and separation magnets 130 may have like poles facing each other (e.g., north poles facing north poles and south poles facing south poles). Anti-virus strips 120 may create a cavity such that inside and outside air is drawn into an interior enclosed space. As will be described in greater detail with respect to FIG. 2, anti-virus strips 120 may be coated with a saline and salt solution for attracting and destroying the coronavirus.

Figure 2:
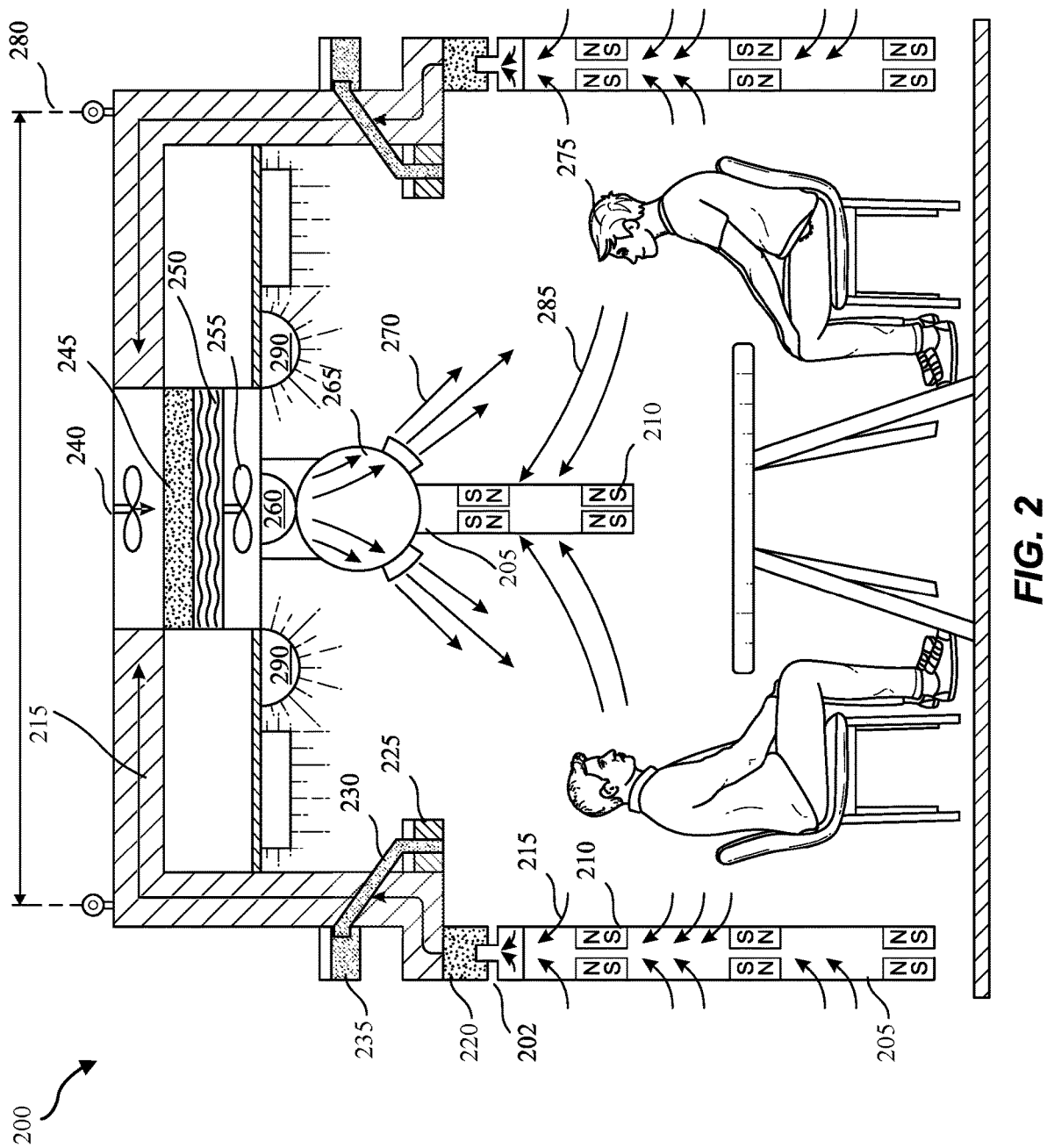
FIG. 2 illustrates a cross-sectional view of the system of FIG. 1, according to an example embodiment.

Turning now to FIG. 2, a cross-sectional view of a coronavirus air sanitization/isolation system with anti-virus curtain walls 200 (i.e., "system 200") is shown. In some embodiments, system 200 may be suspended from a ceiling of an enclosed space (e.g., via suspension cables 280) or alternatively, be installed within an attic above the ceiling of an enclosed space in a building. System 200 may include a group of anti-virus strips 205, a salt filter 220 (i.e., a pass-through salt filter), a wick 230, a saline and soap solution reservoir 225 (utilized for saturating wick 230 with a saline and soap solution), a wick 230, a saline and soap solution reservoir 235 (utilized for saturating wick 230 with a saline and soap solution), a ventilation fan 240, a salt filter 245, an electro-static filter 250, a ventilation fan 255, UV light sources 260 and 290, and a distribution air duct 265. In some examples, exhaust ventilation fan 240 (which may be located in the attic of a building housing an enclosed space containing system 200) may create suction to pull airstream 215 from the below enclosed space and air exterior to the enclosed space. Contaminated airborne droplets in airstream 215 may attach themselves to anti-virus strips 205 which are coated with a saline and soap solution. Then, via osmosis, water may be drawn from the droplets and any virus cells contained therein. Next, soap molecules on anti-virus strips 205 (which, in various embodiments, may be constructed from a translucent material) react to dissolve the fatty layer of the virus thus destroying its ability to replicate in a cell. Any contaminated droplets that do not attach to anti-virus strips 205 may be drawn into air inlet 202 and pass-through salt filter 220. In some embodiments salt filter 220 may be a perforated salt filter.

In some embodiments, the enclosed space surrounded by system 200 may include multiple seated persons 275 separated by anti-virus strips 205 above a shared airspace. In some examples, anti-virus strips 205 separating persons 275 may function as parallel cough and sneeze guard strips. In some examples anti-virus strips 205 separating persons 275 may be either transparent or opaque. In some embodiments, should a person 275 cough or sneeze (and thereby generate an airstream 285), anti-virus strips 205 separating persons 275 may block any contaminated droplets contained in airstream 285 from reaching a person 275 seated across from another person 275. Then, high velocity jet stream air or air jets 270 generated by distribution air duct 265, moving in an opposite direction to airstream 285, may also block any contaminated droplets from moving to a right or left side of a person 275 that coughed or sneezed. As a result, each person 275 may be encased in an air space separated by partitions created by air jets 270. Furthermore, as air jets 270 travel in the enclosed space, after exiting distribution air duct 265, they may expand and become two-dimensional walls due to the entrainment of air in the enclosed space. Thus, air jets 270 may blow past persons 275 and be drawn back into the inlet walls (e.g., air inlet 202) of system 200.

In some examples, system 200 may function to kill or destroy the virus, bacteria, other viruses, and/or spores at multiple locations include anti-virus strips 205, salt filter 220, wick 230 (which is saturated with the saline and soap solution from reservoirs 225 and 235), salt filter 245, electro-static filter 250, and UV light sources 260 and 290. In some examples, UV light source 260 may be installed in distribution air duct 265 and would only be turned on when an airstream (i.e., airstream 215) is flowing through system 200. Additionally, UV light sources 290 (which may be installed in a ceiling of the enclosed space) may only be utilized (i.e.,) when no persons are occupying the enclosed space. Each of UV light sources 260 and 290 may be utilized to disinfect any contaminated surfaces within the enclosed space.

Figure 3:
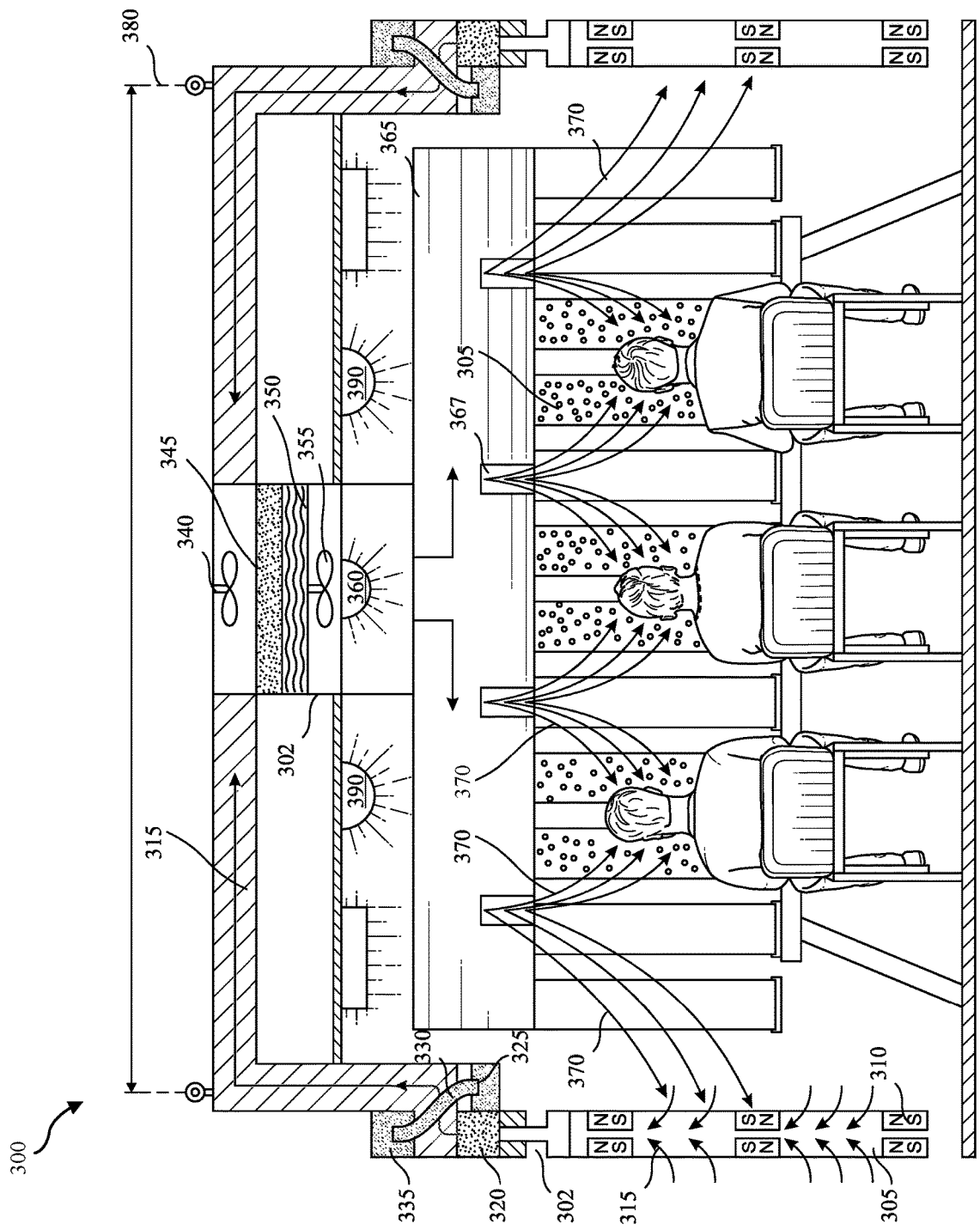
FIG. 3 illustrates a right-side view of the system of FIG. 1, according to an example embodiment.

Turning now to FIG. 3, a right-side view of a coronavirus air sanitization/isolation system with anti-virus curtain walls 300 (i.e., "system 300") is shown. In some embodiments, (and as described above with respect to system 200 of FIG. 2), system 300 may be suspended from a ceiling of an enclosed space (e.g., via suspension cables 380) or alternatively, be installed within an attic above the ceiling of an enclosed space in a building. System 300 may include like components as described above with respect to FIG. 2 including a group of anti-virus strips 305, a salt filter 320, a wick 330, a saline and soap solution reservoir 325 (utilized for saturating wick 330 with a saline and soap solution), a wick 330, a saline and soap solution reservoir 235 (utilized for saturating wick 330 with a saline and soap solution), a ventilation fan 340, a salt filter 345, an electro-static filter 350, a ventilation fan 355, UV light sources 360 and 390, and a distribution air duct 365.

In some examples, distribution air duct 365 may include a set of rectangular air jets slots 367 that are spaced along a length of distribution air duct 365. Air jet slots 367 may be utilized to distribute air in the form of multiple two-dimensional free jets 370 such that each free jet 370 functions as a partition to separate individuals seated below distribution air duct 365 and facing hanging anti-virus strips 305 that have been coated with the saline and salt soap solution discussed above. Thus, should a seated individual sneeze or cough, contaminated droplets would project forward and attach to hanging anti-virus strips 305. Then, via osmosis, water is drawn from the droplets and the virus would then react with the soap molecules within the saline and soap solution coated on anti-virus strips 305. As discussed above, the soap solution would then dissolve the virus fatty layer, thereby destroying the virus and preventing the virus from replicating in a cell. As free jets 370 flow past the individuals in the enclosed space, free jets 370 are then drawn into inlet 302, via airstream 315, of anti-virus strips 305 forming a curtain wall in system 300.

Figure 4:
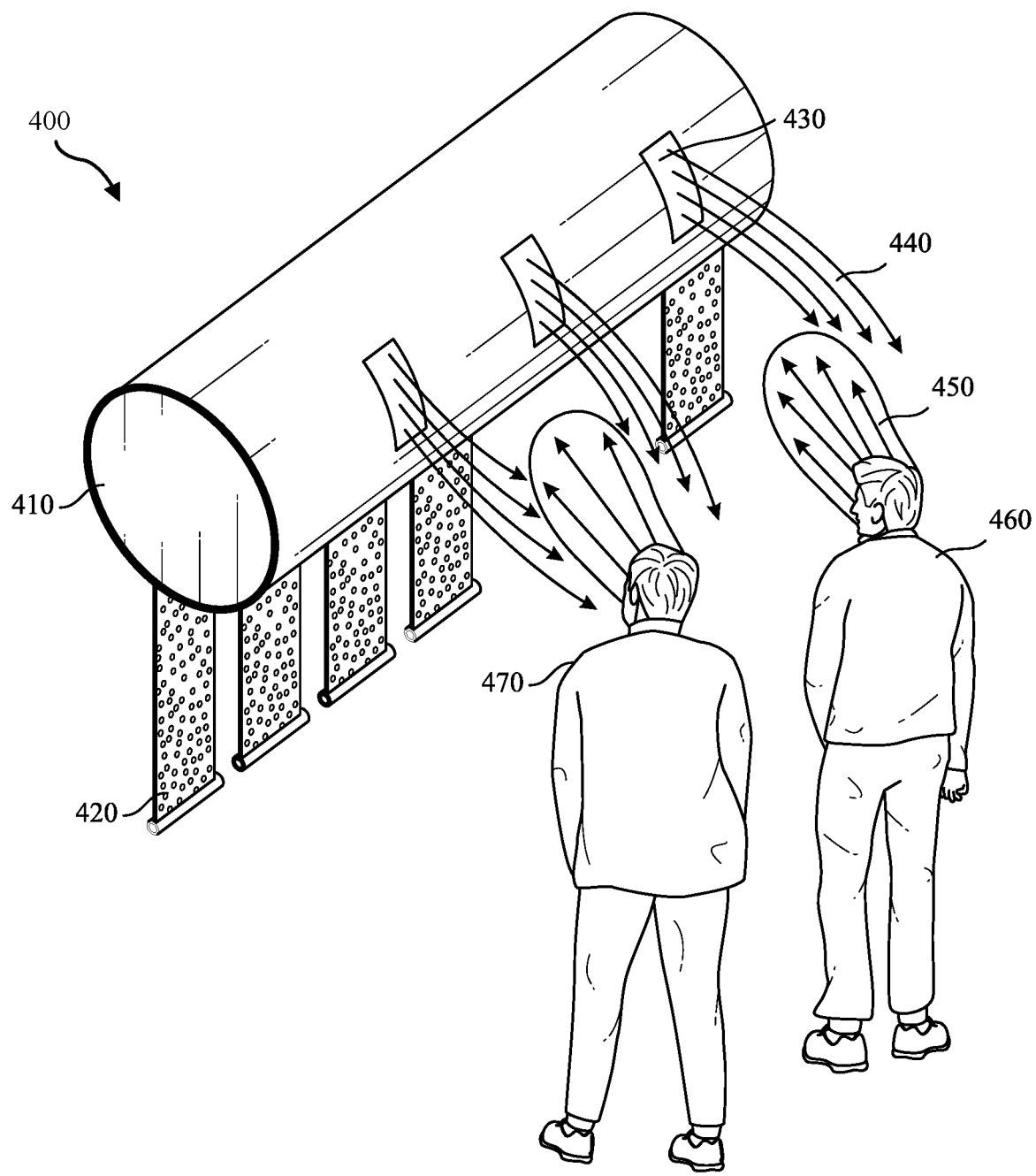
FIG. 4 illustrates a perspective view of a distribution air duct system utilized in the system of FIG. 1, according to an example embodiment.

Turning now to FIG. 4, a perspective view of a distribution air duct system 400 utilized in a coronavirus air sanitization/isolation system with anti-virus curtain walls is shown. Distribution air duct system 400 may include a distribution air duct 410 coupled to a group of anti-virus strips 420. In some embodiments, distribution air duct 410 may include multiple slots 430 from which free air jets 440 may be expelled into an enclosed space. In some examples, slots 430 may be present on both sides (e.g., a front side and a back side) of distribution air duct 410. As discussed above with respect to FIGS. 2-3, free air jets 440 may function as partition walls that essentially isolate persons 460 and 470 within their own areas of uncontaminated air space. Additionally, once free air jets 440 come into contact with anti-virus strips 420, they then become wall jets which flow in an upward direction (i.e., up the wall created by anti-virus strips 420) due to the Coandă effect.

Figure 5:
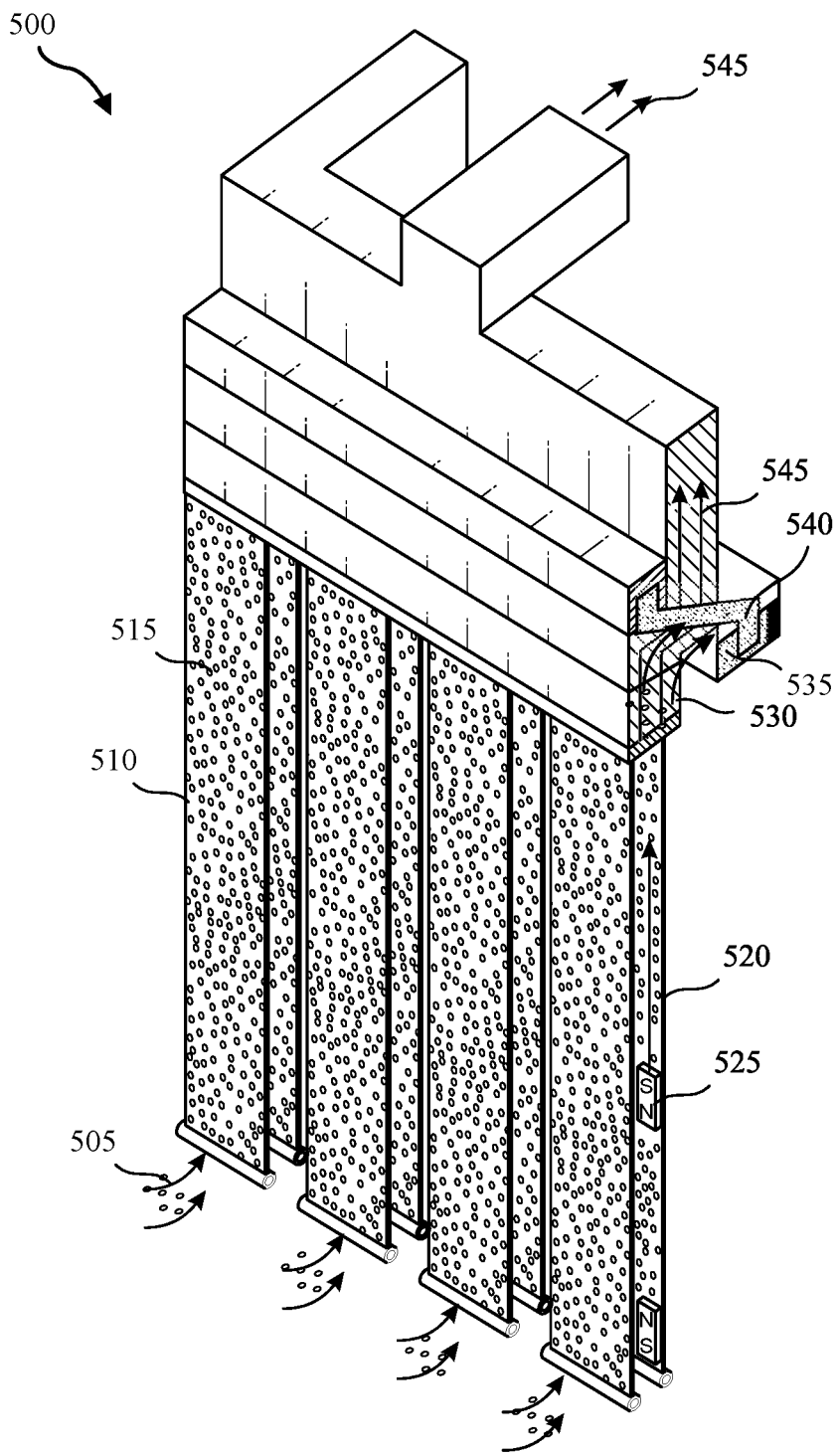
FIG. 5 illustrates a perspective view of an anti-virus curtain wall utilized in the system of FIG. 1, according to an example embodiment.

Turning now to FIG. 5, a perspective view of an anti-virus curtain wall 500 utilized in a coronavirus air sanitization/isolation system with anti-virus curtain walls is shown. In some embodiments, anti-virus curtain wall 500 may include opposing groups of anti-virus strips 510 and 520. Each anti-virus strip 510 and 520 may be coated with a saline and soap solution (as described above with respect to FIGS. 1-3). A set of magnets 525 may be attached to the inside of each of anti-virus strips 510 and 520 to maintain their separation. For example, and as discussed above with respect to separation magnets 130 of FIG. 1, magnets 525 may have opposing polarities (such that north poles face north poles and south poles face south pole) thereby creating a magnetic field to maintain a separation distance between anti-virus strips 510 and 520. As shown in FIG. 5, the curtain wall formed by anti-virus strips 510 and 520 may include attached contaminated droplets 515. As discussed above with respect to FIGS. 2-3, exhaust fans in the coronavirus air sanitization/isolation system with anti-virus curtain walls described herein may pull contaminated air 505 toward the curtain wall formed by anti-virus strips 510 and 520 and into a wall inlet such that any contaminated droplets 515 that are not attracted to anti-virus strips 510 and 520 may pass as an airstream into a perforated salt filter 530 and through a wick 540 (that is saturated with a saline and soap solution stored in reservoir 535) for further decontamination resulting in an uncontaminated air stream 545.

Any process parameters and sequence of steps described and/or illustrated herein are given by way of example only and can be varied as desired. For example, while steps illustrated and/or described herein may be shown or discussed in a particular order, these steps do not necessarily need to be performed in the order illustrated or discussed. Additionally, any exemplary methods described and/or illustrated herein may also omit one or more of steps described or illustrated herein or include additional steps in addition to those disclosed.

The preceding description has been provided to enable others skilled in the art to best utilize various aspects of the exemplary embodiments disclosed herein. This exemplary description is not intended to be exhaustive or to be limited to any precise form disclosed. Many modifications and variations are possible without departing from the spirit and scope of the instant disclosure. The embodiments disclosed herein should be considered in all respects illustrative and not restrictive. Reference should be made to the appended claims and their equivalents in determining the scope of the instant disclosure.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and have the same meaning as the word "comprising."

What is claimed is:

1. A coronavirus air sanitization/isolation system with anti-virus curtain walls, comprising:
   a plurality of anti-virus strips, wherein each of the plurality of anti-virus strips comprise an inner surface and an outer surface, wherein the plurality of anti-virus strips are coated with a saline and soap solution, wherein salt molecules within the saline and soap solution attract airborne droplets contaminated with the coronavirus onto at least one of the inner surface and the outer surface of the anti-virus strips and wherein soap molecules within the saline and soap solution react with the airborne droplets to dissolve a fatty layer of coronavirus cell membranes, thereby destroying the coronavirus;
   a plurality of magnets arranged vertically along a length of the inner surface of each of the anti-virus strips, each of the plurality of magnets comprising a north pole and a south pole, wherein the north poles of a first set of the plurality of magnets face the north poles of a second set of the plurality of magnets and wherein the south poles of the first set of the plurality of magnets faces the south poles of the second set of the plurality of magnets on each of the anti-virus strips, wherein the magnets assist in preventing the anti-virus strips from coming into contact with each other; and an air inlet housing, coupled to a first subset of the anti-virus strips forming a wall of curtains having a confined space, wherein the inlet housing is installed above a ceiling of the confined space and configured to vertically suspend the first subset of the anti-virus strips forming a wall of curtains, the wall of curtains defining an enclosed space, wherein the air inlet housing comprises:
- a first exhaust ventilation fan that utilizes suction to pull air from the confined space into an interior of the enclosed space as an airstream comprising contaminated airborne coronavirus droplets;
- a first salt filter that receives the airstream from the first exhaust ventilation fan;
- a wick saturated with the saline and soap solution that receives the airstream from the first salt filter, wherein the soap molecules within the saline and soap solution dissolve a fatty layer of coronavirus cell membranes within the airstream, thereby destroying the coronavirus;
- a second salt filter below the first exhaust ventilation fan that receives the airstream from the first exhaust ventilation fan;
- an electro-static air filter below the second salt filter that receives the airstream from the second salt filter;
- a second exhaust ventilation fan below the electro-static air filter that receives the airstream from the electro-static air filter;
- a distribution air duct below the second exhaust ventilation fan that receives the airstream from the second exhaust ventilation fan, wherein the distribution air duct comprises a plurality of air jet slots spaced along a length of the distribution air duct, wherein the air jet slots distribute the airstream as a plurality of free jets, and wherein the distribution air duct comprises an ultra-violet (UV) light source that generates UV radiation for disinfecting one or more contaminated surfaces in the enclosed space; and
- a second subset of the plurality of anti-virus strips coupled to the distribution air duct and vertically suspended between each of a pair of opposing air jet slots in the plurality of air jet slots, wherein the second subset of the plurality of anti-virus strips face each of one or more persons in the enclosed space for intercepting contaminated airborne coronavirus droplets expelled from the one or more persons in the enclosed space, and wherein the second subset of anti-virus strips are coated with the saline and soap solution.

2. The system of claim 1, further comprising a plurality of additional UV light sources mounted within a ceiling of the enclosed space and proximate to the distribution air duct, wherein the additional UV light sources are utilized to generate UV radiation for disinfecting the contaminated surfaces in the enclosed space only when the persons occupying the enclosed space have exited the enclosed space.

3. The system of claim 1, wherein the saline and soap solution on the surface of the anti-virus strips draws, via osmosis, water from the airborne droplets contaminated with the coronavirus.

4. The system of claim 1, wherein the dissolved fatty layer of the coronavirus cell membranes by the soap molecules prevent cell replication of the coronavirus.

5. The system of claim 1, wherein any remaining airborne droplets in the airstream that are not attracted to the surface of the anti-virus strips are drawn into the first exhaust ventilation fan.

6. The system of claim 1, wherein the saline and soap solution saturates the wick with water molecules and heat in the airstream evaporates the water molecules in the wick and raises a relative humidity of the airstream.

7. The system of claim 1, wherein the second salt filter, upon receiving the airstream from the first exhaust ventilation fan, lowers a relative humidity of the airstream.

8. The system of claim 1, wherein the electro-static filter, upon receiving the airstream from the second salt filter, removes one or more of salt residue particles, dust particles, and spores from the airstream.

9. The system of claim 1, wherein the UV light source only generates the UV radiation for disinfecting the one or more contaminated surfaces in the enclosed space when the airstream is flowing through the air inlet housing.

10. The system of claim 1, wherein each of the plurality of free jets comprises distributed air that envelops each of the one or more persons occupying the enclosed space within an uncontaminated zone of air.

11. The system of claim 1, wherein the plurality of free jets is converted into a plurality of wall jets upon coming into contact with the plurality of anti-virus strips.

12. The system of claim 1, wherein the second subset of the plurality of anti-virus strips intercept the contaminated airborne coronavirus droplets by receiving one or more coughs and sneezes expelled from the one or more persons in the enclosed space.

13. A coronavirus air sanitization/isolation system with anti-virus curtain walls, comprising:
- a plurality of anti-virus strips, wherein each of the plurality of anti-virus strips comprise an inner surface and an outer surface, wherein the plurality of anti-virus strips are coated with a saline and soap solution, wherein salt molecules within the saline and soap solution attract airborne droplets contaminated with the coronavirus onto at least one of the inner surface and the outer surface of the anti-virus strips and wherein soap molecules within the saline and soap solution react with the airborne droplets to dissolve a fatty layer of coronavirus cell membranes, thereby destroying the coronavirus;
- a plurality of magnets arranged vertically along a length of the inner surface of each of the anti-virus strips, each of the plurality of magnets comprising a north pole and a south pole, wherein the north poles of a first set of the plurality of magnets face the north poles of a second set of the plurality of magnets and wherein the south poles of the first set of the plurality of magnets faces the south poles of the second set of the plurality of magnets on each of the anti-virus strips, wherein the magnets assist in preventing the anti-virus strips from coming into contact with each other;
- an air inlet housing, coupled to a first subset of the anti-virus strips forming a wall of curtains having a confined space, wherein the inlet housing is installed above a ceiling of the confined space and configured to vertically suspend the first subset of the anti-virus strips forming a wall of curtains, the wall of curtains defining an enclosed space, wherein the air inlet housing comprises:
  a first exhaust ventilation fan that utilizes suction to pull air from the confined space into an interior of the enclosed space as an airstream comprising contaminated airborne coronavirus droplets;
  a first salt filter that receives the airstream from the first exhaust ventilation fan;
  a wick saturated with the saline and soap solution that receives the airstream from the first salt filter, wherein the soap molecules within the saline and soap solution dissolve a fatty layer of coronavirus cell membranes within the airstream, thereby destroying the coronavirus;
  a second salt filter below the first exhaust ventilation fan that receives the airstream from the first exhaust ventilation fan;
  an electro-static air filter below the second salt filter that receives the airstream from the second salt filter;
  a second exhaust ventilation fan below the electro-static air filter that receives the airstream from the electro-static air filter;
  a distribution air duct below the second exhaust ventilation fan that receives the airstream from the second exhaust ventilation fan, wherein the distribution air duct comprises a plurality of air jet slots spaced along a length of the distribution air duct, wherein the air jet slots distribute the airstream as a plurality of free jets, wherein each of the plurality of free jets comprises distributed air that envelops each of one or more persons occupying the enclosed space within an uncontaminated zone of air, wherein the plurality of free jets is converted into a plurality of wall jets upon coming into contact with the plurality of anti-virus strips, wherein the distribution air duct comprises an ultra-violet (UV) light source that generates UV radiation for disinfecting one or more contaminated surfaces in the enclosed space, and wherein the UV light source only generates the UV radiation for disinfecting the one or more contaminated surfaces in the enclosed space when the airstream is flowing through the air inlet housing; and
  a second subset of the plurality of anti-virus strips coupled to the distribution air duct and vertically suspended between each of a pair of opposing air jet slots in the plurality of air jet slots, wherein the second subset of the plurality of anti-virus strips face each of the one or more persons in the enclosed space for intercepting contaminated airborne coronavirus droplets expelled from the one or more persons in the enclosed space, and wherein the second subset of anti-virus strips are coated with the saline and soap solution; and
a plurality of additional UV light sources mounted within the ceiling and proximate to the distribution air duct, wherein the additional UV light sources are utilized to generate UV radiation for disinfecting the contaminated surfaces in the enclosed space only when the persons occupying the enclosed space have exited the enclosed space.

\* \* \* \* \*